United States Patent
Kwiatkowski et al.

(10) Patent No.: US 6,307,050 B1
(45) Date of Patent: Oct. 23, 2001

(54) METHOD OF SYNTHESIZING FLOSEQUINAN FROM 4-FLUOROANTHRANILIC ACID

(75) Inventors: Stephan Kwiatkowski, Lexington; Maya Siddidqui, Liberty; Rodney Eisenberg, Richmond; Sudarsan Mukhopadhyay, Lexington; Lowell Jeffry Lawrence, Lexington; Steven G. Mobley, Lexington, all of KY (US)

(73) Assignee: R. T. Alamo Venture I LLC, Beverly Hills, CA (US)

( * ) Notice: Subject to any disclaimer, the term of this patent is extended or adjusted under 35 U.S.C. 154(b) by 0 days.

(21) Appl. No.: 09/779,136

(22) Filed: Feb. 7, 2001

Related U.S. Application Data

(60) Provisional application No. 60/228,667, filed on Aug. 29, 2000.

(51) Int. Cl.[7] .................................................. C07D 215/36
(52) U.S. Cl. .............................................................. 546/155
(58) Field of Search ............................................... 546/155

(56) References Cited

U.S. PATENT DOCUMENTS 4,302,460  *  11/1981  Davies et al. ..................... 424/258

* cited by examiner

*Primary Examiner*—Patricia L. Morris
(74) *Attorney, Agent, or Firm*—Milbank, Tweed, Hadley & McCloy LLP

(57) ABSTRACT

A high-yield, 4-step synthesis for flosequinan

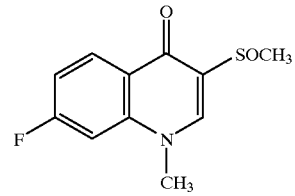

starting with 4-fluoroanthranilic acid comprising cyclization with phosgene to create an intermediate -A, followed by methylation to create an intermediate -B, then by reaction with dimsyl sodium to create an intermediate -C, then by reaction with triethyl orthoformate in the presence of piperdine and acetic acid to give flosequinan. The overall yield of the disclosed process is greater than about 16%.

8 Claims, No Drawings

METHOD OF SYNTHESIZING FLOSEQUINAN FROM 4-FLUOROANTHRANILIC ACID

This application claims benefit of Provisional application No. 60/228,667, filed Aug. 29, 2000.

FIELD OF THE INVENTION

The invention is directed to a novel synthetic process for the manufacture of flosequinan, 7-fluoro-1-methyl-3-methylsulphinyl-4-quinolone, starting with 4-fluoroanthranilic acid.

BACKGROUND OF THE INVENTION

Flosequinan is one of a class of quinoline compounds having therapeautic potential as antihypertensive agents or in the treatment of heart failure. Recently, flosequinan has been found potentially useful in the treatment of erectile dysfunction, as disclosed in commonly owned U.S. Pat. No. 6,110,489 and patent application Ser. No. 09/166,703, the contents of which are incorporated by reference herein.

The synthesis of flosequinan has been discussed in the literature and has been the subject of several patents. In Birch et al., *Synthesis of Flosequinan: A Novel 4-Quinolone shown to be useful in Congestive Heart Failure*, J. Chem. Soc. Perkins Trans. 1994, 387–392, the authors describe two approaches to the synthesis of flosequinan and its metabolite, flosequinoxan. The first approach was used in part by the inventors in developing the novel pathway disclosed herein. However, there are several significant differences and improvements in the novel pathway disclosed by the inventors herein, which result in high yields and purity as compared to the prior art.

Some of the authors of the above literature reference are named as inventors on several patents, including U.S. Pat. Nos. 5,011,931 and 5,079,264 and European Patent No. 0135367. These three patents include various synthetic steps that have been used historically in the synthesis of flosequinan. These patents do not, however, disclose or suggest the inventive pathway described by the inventors herein.

Other literature references relating to the synthesis and characterization of flosequinan include Kashiyama et. al., *Stereoselective S-Oxidation of Flosequinan Sulfide By Rat Hepatic Flavin-Containing Monooxygenase 1A1 Expressed in Yeast*, Biochemical Pharmacology, Vol. 47, No. 8, 1357–1363 (1994); Russell et. al., *The Synthesis of 2,3-Ring-Fused Analognues of 7-Flouro-1-methyl-3-(methylsulfinyl)-4(1H)-quinoline*, Synthesis, 753–755 (August 1992), and Morita et. al., *Synthesis and Absolute Configuration of the Enantiomers of 7-Flouro-1-methyl-3-(methylsulfinyl)-4(1H)-quinoline (Flosequinan)*, Chem. Pharm. Bull. 42(10), 2157–2160 (1994). The last of these references addresses synthesis of optically active flosequinan via diastereomeric separation of certain (R)-methylbenzylamine derivatives and the determination of their absolute configuration by X-ray crystallographic analysis.

SUMMARY OF THE INVENTION

The inventive process is a 4-step pathway for the high-yield synthesis of flosequinan starting from 4-fluoroanthranilic acid. In the inventive process, the starting material (formula I):

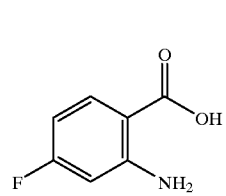

is cyclized by reaction with phosgene to form intermediate-A, 4-fluoro-anthranilic acid isatoic anhydride (formula II):

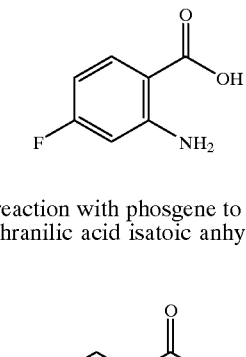

which is then methylated using a source of methyl groups such as dimethyl sulfate to form intermediate-B, N-methyl-4-fluro-anthranilic acid isatoic anhydride (formula III):

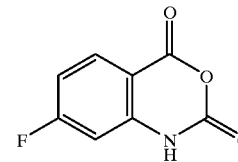

which is then reacted with dimsyl sodium to produce intermediate-C, 1-(4-fluoro-2-methylaminophenyl)-2-methylsulfinylethanone (formula IV):

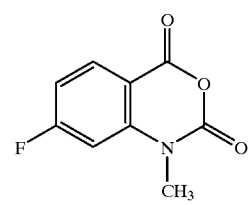

which is then treated with triethyl orthoformate in the presence of piperidine and acetic acid to produce flosequinan, 7-fluoro-1-methyl-3-methylsulfinyl-4-quinolone (formula V):

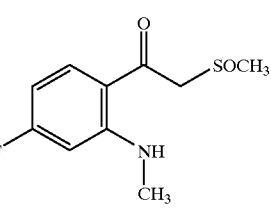

DETAILED DESCRIPTION OF THE INVENTION

To disclose and illustrate the invention, a proposed scale-up procedure based on a successful 1-gram batch was filed as provisional patent application Ser. No. 60/228,667, which is expressly incorporated by reference herein. A 500 gram batch of flosequinan was subsequently prepared using the inventive 4-step process according to the following procedure. This procedure serves as an non-limitative example of the inventive process, and constitutes the inventors' best known mode for making and using the invention.

Step I

In a clean and dry 12 liter glass reactor equipped with a back suction trap plus a NaOH (25%) trap at the outlet and a back suction trap in the inlet, 3.840 liters of toluene were charged and cooled to −45° C. using a dry ice-acetone bath. Using appropriate safety precautions, 832 gm of phosgene were then passed through the cold toluene while stirring to prepare a 20% (wt/wt) solution. The addition of the phosgene took approximately 3.5 hours.

Separately, into a clean and dry 22 liter glass reactor equipped with the above-described types of back suction traps, 399 g of starting material (formula I) was added with stirring to 4.37 liters of deionized water. A separate 6.8% solution of sodium carbonate in water was also prepared by adding 297 g of sodium carbonate to 4.37 liters of deionized water. Using a clean addition funnel, the sodium carbonate solution was then slowly added with stirring to the suspension of the starting material, to create a brown-colored solution.

In preparation for the reaction step, the phosgene solution was warmed from −45° C. to −15° C. and the mixture of the starting material and the sodium carbonate was cooled to 10° C. The phosgene solution was then added over approximately 1.5 hours with stirring to the brown solution. The reaction mixture was stirred overnight allowing the desired intermediate-A (formula II) to precipitate out. A sample was removed for NMR assessment and the precipitate was filtered on a 4 liter sintered glass funnel. The filtrate was washed with 2×500 ml aliquots of cold deionized water and dried under a vacuum at approximately 50° C. for 16 hours.

A 93.4% lot yield of 435 g of intermediate-A (formula II) was obtained. This procedure was repeated three more times, starting with approximately 400 g of starting material each time. Lot yields of 448 g (94.5%), 449 g (95.9%), and 459 g (96.8%) were obtained.

Step II

In a 22 L oven dried glass reactor equipped with a reflex condenser, addition funnel and temperature recorder, 11.40 liters of anhydrous tetrahydrofuran (THF) were added under nitrogen. To this reactor were also added 409 g of 60% sodium hydride in oil. Eight approximately equal portions of intermediate-A (formula II) were then added to the reactor, totaling 883 g altogether. As this reaction is exothermic, care was taken to avoid excessive heat and bubbling. Final temperature was 40° C., with a maximum observed temperature of 41° C. The reaction mixture was stirred until hydrogen gas evolution ceased.

To the reaction mixture was then slowly added 575 ml (766.4 g) of dimethyl sulfate, keeping the temperature below 50° C. Upon completion, the reaction mixture was stirred at 50° C. for 3 hours with the reflux condenser on. A sample was removed for NMR assessment, and the heat was turned off before stirring overnight.

In the morning, the stirring was stopped and the clear liquid on top was siphoned off. This liquid was filtered using a 2–3 inch thick Celite pad in a 2 liter sintered glass funnel. The residue cake was kept covered to minimize contact with atmospheric moisture. The residue was collected and washed with 4 aliquots of anhydrous THF. The filtrate and the washings were evaporated to dryness using a rotary evaporator and the residue obtained was dried under vacuum at approximately 36–38° C. overnight. A sample was removed for NMR assessment of the amount of unreacted dimethyl sulfate present. The dried residue was then added to 1600 ml of a 1:3 toluene:hexane mixture and vigorously stirred. This mixture was then filtered and washed with 2×700 ml washings of 1:3 toluene:hexane mixture. A reference sample was removed for NMR assessment and the residue was dried at 51–50° C. under vacuum for 36 hours.

This batch yielded 871 g of intermediate-B (formula III) for a lot yield of 91.6%. Another 907.1 g of intermediate-A was subjected to the procedure of step II, in which the amounts of reactants and solvents was proportionately adjusted with a yield of 850 g (87%).

Step III

In an oven dried 12 liter glass reactor equipped with a stirrer, temperature recorder and addition funnel, 2550 ml of anhydrous toluene was added under nitrogen. Then 236 g of 60% sodium hydride in oil was added, all at room temperature. The reaction mixture was heated with continuous stirring to 75° C. using a heating mantel. Then 1.59 liters of anhydrous dimethyl sulfoxide (DMSO) were added slowly and carefully over 45 minutes taking care to avoid excessive bubbling. The reaction mixture was stirred for one hour at 70–72° C. until clear and hydrogen gas evolution ceased. The heating mantel was turned off and a water bath was used to cool the reaction mixture to 30° C.

To this mixture, 538.2 g of dry intermediate-B (formula III) was added slowly in portions, keeping the temperature no higher than 35° C. Then 1.9 liters of anhydrous DMSO was added, again keeping the temperature no higher than 35° C. The reaction mixture was stirred under nitrogen for one hour, allowing the mixture to cool to 26°. The reaction mixture was then quenched slowly and carefully with 320 ml of methanol. The resulting suspension was then added slowly and with vigorous stirring to a 22 liter reaction vessel containing 12.760 liters of diethyl ether.

After stirring was stopped, the upper ether layer was siphoned off and the brown oil lower layer was washed with 520 ml of fresh ether. The oily yellow residue was triturated with 2600 ml of deionized water until a yellow precipitate formed. This precipitate was filtered using a 2 liter sintered glass funnel and the solid residue was washed with three aliquots of 130 ml cold deionized water. A reference sample was taken to assess the residue. The residue was dried under vacuum at 50–53° C. for 23 hours.

This procedure produced 243 g of intermediate-C (formula IV), a 38.4% yield. Two other batches of intermediate-B were treated according to this Step III procedure, with proportionate adjustments to the amounts of reactants and solvents. The first additional batch of 538.2 g intermediate-B produced a 192 g (30.4%) yield, and the second additional batch of 87.38 g of intermediate-B produced a yield of 42 g (40.9%).

Step IV

In a 12 liter oven dry glass reactor equipped with a stirrer, temperature recorder and addition funnel which has been dried by nitrogen flow for 30 minutes the following chemicals were charged: 7.990 liters of triethyl orthoformate; 696 g of intermediate-C; 324 ml of piperdine; and 296 ml of acetic acid. The reaction mixture was heated under nitrogen to reflux at approximately 105° C. for 2 hours. A sample was removed to assess the progress of the reaction step by NMR.

Using a water bath, the reaction mixture was then cooled to room temperature and stirred for 30 minutes. The final product precipitated out and was collected by filtration on a 4 liter sintered glass funnel. The residue was washed with 3×700 ml aliquots of diethyl ether, and a sample was removed for NMR assessment. The residue was dried under vacuum at 50–51° C. for 17 hours. A sample of the dried flosequinan product (formula V) was removed for NMR assessment. 547 g (75.3%) yield of flosequinan was obtained (an additional 47 g of product was scraped from the bottom of the sintered glass filter but was not included in this total yield calculation).

We claim:

1. A process to prepare a compound of formula V comprising the following steps:

(a) Cyclizing a compound of formula I:

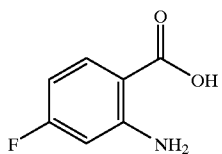

by reaction with phosgene to give a compound of formula II:

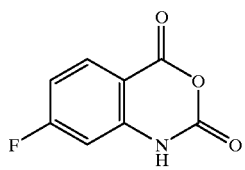

(b) reacting the product of step (a) with a methylating agent to give a compound of formula III:

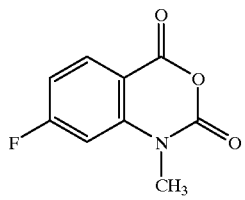

(c) reacting the product of stage (b) with dimsyl sodium to give a compound of formula IV:

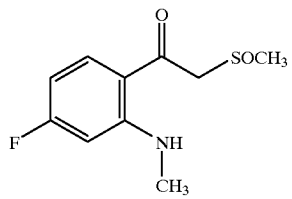

and (d) treating the product of stage (c) with triethyl orthoformate in the presence of piperdine and acetic acid to give the compound of formula V:

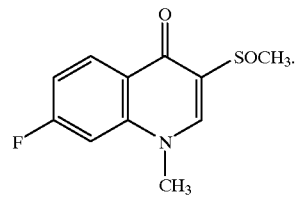

2. The process according to claim 1, in which step (a) comprises creating an approximately 20% (wt/wt) solution of phosgene in toluene, an approximately 6.8% solution of sodium carbonate in water, mixing the sodium carbonate solution with an aqueous solution of formula I, and then adding the phosgene solution to the solution of sodium carbonate and formula I.

3. The process according to claim 2, wherein the yield for step (a) is greater than about 90%.

4. A process according to claim 1 in which step (b) comprises reacting the product of step (a) with a suspension of sodium hydride in tetrahydrofuran and dimethyl sulfate.

5. The process according to claim 4, wherein the yield for step (b) is greater than about 85%.

6. A process according to claim 1 in which step (c) comprises reacting the product of step (b) with a suspension of sodium hydride in toluene and dimethyl sulfoxide.

7. The process according to claim 6, wherein the yield for step (c) is greater than about 30%.

8. The process according to claim 1, wherein the yield for step (d) is greater than about 70%.

* * * * *